United States Patent
Blaskovics et al.

(10) Patent No.: US 8,897,532 B2
(45) Date of Patent: Nov. 25, 2014

(54) SYSTEMS AND METHODS FOR PERFORMING IMAGE TYPE RECOGNITION

(75) Inventors: Tamas Blaskovics, Csongrad (HU); Ferenc Kovacs, Kecskemet (HU); Andras Kriston, Mako (HU)

(73) Assignee: General Electric Company, Schenectady, NY (US)

( * ) Notice: Subject to any disclaimer, the term of this patent is extended or adjusted under 35 U.S.C. 154(b) by 184 days.

(21) Appl. No.: 13/546,189

(22) Filed: Jul. 11, 2012

(65) Prior Publication Data

US 2014/0016846 A1 Jan. 16, 2014

(51) Int. Cl.
*G06K 9/00* (2006.01)

(52) U.S. Cl.
USPC .......................................... 382/131; 382/128

(58) Field of Classification Search
None
See application file for complete search history.

(56) References Cited

U.S. PATENT DOCUMENTS

| 7,792,339 | B2 | 9/2010 | Li |
| 2007/0076938 | A1 | 4/2007 | Hartman et al. |
| 2007/0109402 | A1* | 5/2007 | Niwa ................................ 348/77 |
| 2009/0156947 | A1 | 6/2009 | Seward et al. |
| 2012/0224759 | A1* | 9/2012 | Masui et al. .................. 382/131 |

OTHER PUBLICATIONS

Michal Sofka, et al "Automatic Contrast Phase Estimation in CT Volumes", Image Anaytics and Informatics Siemens Corporation Research, Princeton, N J, USA, 2011.*
DJ Withey, "Medical Image Segmentation: Methods and Software", Proceedings of NFSI & ICFBI 2007 and Hangzhou, China, Oct. 12-14, 2007.
Thomas M. Lehmann, et al, "IRMA—Content Based Image Retrival in Medical Applications" MEDINFO 2004.
T.M. Lehmann, et al, "Content-based Image Rerival in Medical Application", 2004 Schattauer GmbH.
Michal Sofka, et al "Automatic Contrast Phase Estimation in CT Volumes", Image Anaytics and Informatics Siemens Corporation Research, Princeton, NJ, USA, 2011.

* cited by examiner

*Primary Examiner* — Amara Abdi
(74) *Attorney, Agent, or Firm* — Dean D. Small; The Small Patent Law Group

(57) ABSTRACT

A method for determining image information for an image of an object includes obtaining at least one image of an object of interest, automatically determining an image type and a presence or absence of a contrast agent, automatically generating a label that indicates the image type and the presence or absence of the contrast agent, and modifying the at least one image to include the label. A system and non-transitory computer readable medium are also described herein.

17 Claims, 7 Drawing Sheets

SYSTEMS AND METHODS FOR PERFORMING IMAGE TYPE RECOGNITION

BACKGROUND OF THE INVENTION

The subject matter described herein relates generally to imaging systems, and more particularly, to systems and methods for performing image type recognition.

Imaging systems are widely used to generate images of various anatomical features or objects of interest. For example, in an oncology examination, a patient may go through a series of examinations, using for example, a computed tomography (CT) system, a positron emission tomography (PET) system, an ultrasound system, an x-ray system, a magnetic resonance (MR) system, a single photon emission computed tomography (SPECT) system, and/or other imaging systems. The series of examinations is performed to continuously monitor the patient's response to treatment. The images acquired during the examination may be displayed or saved to enable a physician to perform a diagnosis of the patient. Thus, the patient is typically scanned with an imaging system selected to provide the most relevant images needed by the physician to perform the medical diagnosis.

Additionally, in some clinical procedures, the patient may be injected with a contrast agent such that when the patient is scanned, the resultant images provide additional information that is relevant to the diagnosis. Accordingly, in operation a patient may be scanned using a variety of imaging modalities. Moreover, the patient may be scanned with or without the use of a contrast agent. Because, a typical patient may be scanned using a variety of imaging modalities and with or without a contrast agent, the user performing the scanning procedure manually labels the acquired images to denote, among other things, the modality of imaging system used to acquire the images and whether the acquired images include contrast agent information or do not include contrast agent information.

However, manually labeling the images requires significant manual input. For example, inputting the image labels is performed manually by the user to denote the imaging modality utilized to generate the images and the use of the contrast agent. As a result, manually inputting the labels on the images is relatively time consuming. Moreover, because the labels are entered manually, the labels may include errors. For example, the label on a particular image may incorrectly state the modality used to acquire the image. Additionally, the label may incorrectly state that a contrast agent was utilized when a contrast agent was not utilized. Accordingly, the incorrectly labeled images may lengthen a time for the physician to perform the diagnosis of the patient.

SUMMARY OF THE INVENTION

In one embodiment, a method for determining image information for an image of an object is provided. The method includes obtaining at least one image of an object of interest, automatically determining an image type and a presence or absence of a contrast agent, automatically generating a label that indicates the image type and the presence or absence of the contrast agent, and modifying the at least one image to include the label.

In another embodiment, an imaging system is provided. The imaging system includes an imaging scanner and a processor coupled to the imaging scanner. The processor is configured to obtain at least one image of an object of interest, automatically determine an image type and a presence or absence of a contrast agent, automatically generate a label that indicates the image type and the presence or absence of the contrast agent, and modify the at least one image to include the label.

In a further embodiment, a non-transitory computer readable medium is provided. The non-transitory computer readable medium is programmed to instruct a computer to obtain at least one image of an object of interest, automatically determine an image type and a presence or absence of a contrast agent, automatically generate a label that indicates the image type and the presence or absence of the contrast agent, and modify the at least one image to include the label.

DETAILED DESCRIPTION OF THE INVENTION

Figure 1:
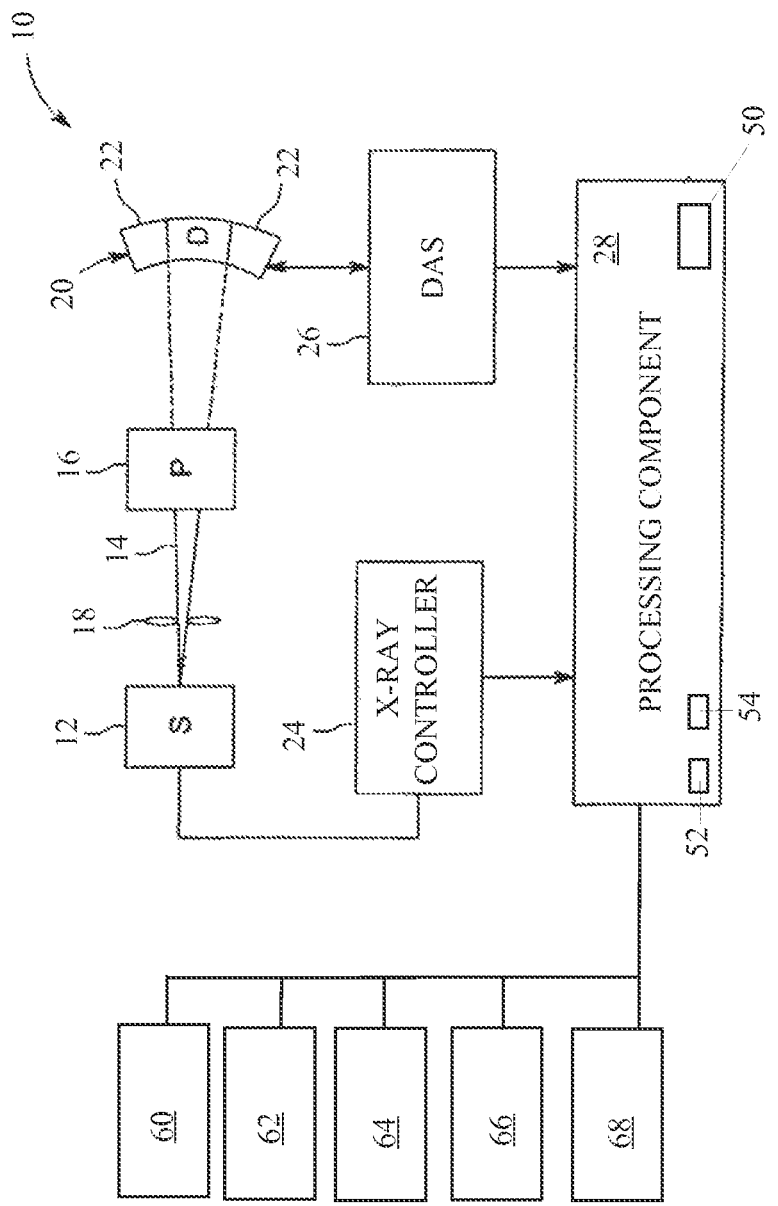
FIG. 1 is a simplified block diagram of a computed tomography (CT) imaging system that is formed in accordance with various embodiments

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Although various embodiments are described with respect to a computed tomography (CT) imaging system, it should be noted that various embodiments, including the method and system for automatically generating an image viewing window described herein may be modified for use with other imaging systems. For example, the method and system may be utilized with a positron emission tomography (PET) system, a single photon emission computed tomography (SPECT) system, a magnetic resonance imaging (MR) system, an ultrasound imaging system, and/or an x-ray system, among others.

In various embodiments, a method and/or system is provided that automatically identifies an image type, e.g., the modality utilized to acquire the image, and whether the image has been enhanced via a contrast agent based on the image data itself. Using the methods and systems described herein an automatic segmentation of an anatomical region may be computed in the background, for example at night or when the computation resources are available. As a result, when a clinician loads the medical images the computed segmentations are immediately visually observable by the clinician. The resultant images may then be utilized for radiation treatment, surgery planning and many other general clinical workflow applications to delineate a contour or a major part of an anatomical structure on a large number of two-dimensional (2D), three-dimensional (3D) and/or four-dimensional (4D) images.

The methods described herein may be performed automatically by the systems described herein to significantly decrease a processing time of the images. More specifically, in various embodiments, the image data itself is analyzed to generate information that is subsequently utilized to generate a label, such as a Digital Imaging and Communications in Medicine (DICOM) tag that is automatically formed on or associated with the image. A technical effect of various embodiments is to automatically generate a DICOM tag or label to enable the clinician to identify the imaging modality utilized to generate the image and information that indicates whether the image includes information representative of a contrast agent.

FIG. 1 is a simplified block diagram of an imaging system 10 that is formed in accordance with various embodiments. Although the illustrated embodiment is described with respect to a CT imaging system 10, it should be realized that the methods described herein may be utilized with any imaging system.

Accordingly, in the illustrated embodiment, the imaging system 10 includes an x-ray source 12 that is configured to emit radiation, e.g., x-rays 14, through a volume containing a subject 16, e.g. a patient being imaged. In the embodiment shown in FIG. 1, the imaging system 10 also includes an adjustable collimator 18. In operation, the emitted x-rays 14 pass through an opening of the adjustable collimator 18 which limits the angular range associated with the x-rays 14 passing through the volume in one or more dimensions. More specifically, the collimator 18 shapes the emitted x-rays 14, such as to a generally cone or generally fan shaped beam that passes into and through the imaging volume in which the subject 16 is positioned. The collimator 18 may be adjusted to accommodate different scan modes, such as to provide a narrow fan-shaped x-ray beam in a helical scan mode and a wider cone-shaped x-ray beam in an axial scan mode. The collimator 18 may be formed, in one embodiment, from two cylindrical disks that rotate to adjust the shape or angular range of the x-rays 14 that pass through the imaging volume. Optionally, the collimator 18 may be formed using two or more translating plates or shutters. In various embodiments, the collimator 18 may be formed such that an aperture defined by the collimator 18 corresponds to a shape of a radiation detector 20.

In operation, the x-rays 14 pass through or around the subject 16 and impinge on the detector 20. The detector 20 includes a plurality of detector elements 22 that may be arranged in a single row or a plurality of rows to form an array of detector elements 22. The detector elements 22 generate electrical signals that represent the intensity of the incident x-rays 14. The electrical signals are acquired and processed to reconstruct images of one or more features or structures within the subject 16. In various embodiments, the imaging system 10 may also include an anti-scatter grid (not shown) to absorb or otherwise prevent x-ray photons that have been deflected or scattered in the imaging volume from impinging on the detector 20. The anti-scatter grid may be a one-dimensional or two-dimensional grid and/or may include multiple sections, some of which are one-dimensional and some of which are two-dimensional.

The imaging system 10 also includes an x-ray controller 24 that is configured to provide power and timing signals to the x-ray source 12. The imaging system 10 further includes a data acquisition system 26. In operation, the data acquisition system 26 receives data collected by readout electronics of the detector 20. The data acquisition system 26 may receive sampled analog signals from the detector 20 and convert the data to digital signals for subsequent processing by a processor 28. Optionally, the digital-to-analog conversion may be performed by circuitry provided on the detector 20.

The processor 28 is programmed to perform functions described herein, and as used herein, the term processor is not limited to just integrated circuits referred to in the art as computers, but broadly refers to computers, microcontrollers, microcomputers, programmable logic controllers, application specific integrated circuits, and other programmable circuits, and these terms are used interchangeably herein. The processor 28 may be embodied as any suitably appropriate computing device, e.g., a computer, personal digital assistant (PDA), laptop computer, notebook computer, a hard-drive based device, smartphone, or any device that can receive, send, and store data.

The imaging system 10 also includes an image type recognition module 50 that is configured to receive an image or a series of images, such as a series of images 52, and implement various methods described herein. For example, the anatomical image type recognition module 50 may be configured to automatically generate information that is subsequently utilized to generate a label, such as a DICOM tag 54 that is automatically formed on or associated with the image. The DICOM tag 54 includes information that enables a clinician to identify the imaging modality utilized to generate the image and information that indicates whether the image includes information representative of a contrast agent.

The image type recognition module 50 may be implemented as a piece of hardware that is installed in the processor 28. Optionally, the image type recognition module 50 may be implemented as a set of instructions that are installed on the processor 28. The set of instructions may be stand alone programs, may be incorporated as subroutines in an operating system installed on the processor 28, may be functions that are installed in a software package on the processor 28, or may be a combination of software and hardware. It should be understood that the various embodiments are not limited to the arrangements and instrumentality shown in the drawings.

As shown in FIG. 1, the image type recognition module 50 may also be utilized to create a DICOM tag for images acquired from other imaging modalities. For example, the image type recognition module 50 may receive information from a PET system 60, an ultrasound system 62, an x-ray system 64, a MR system 66, a SPECT system 68, and/or other imaging systems.

Figure 2:
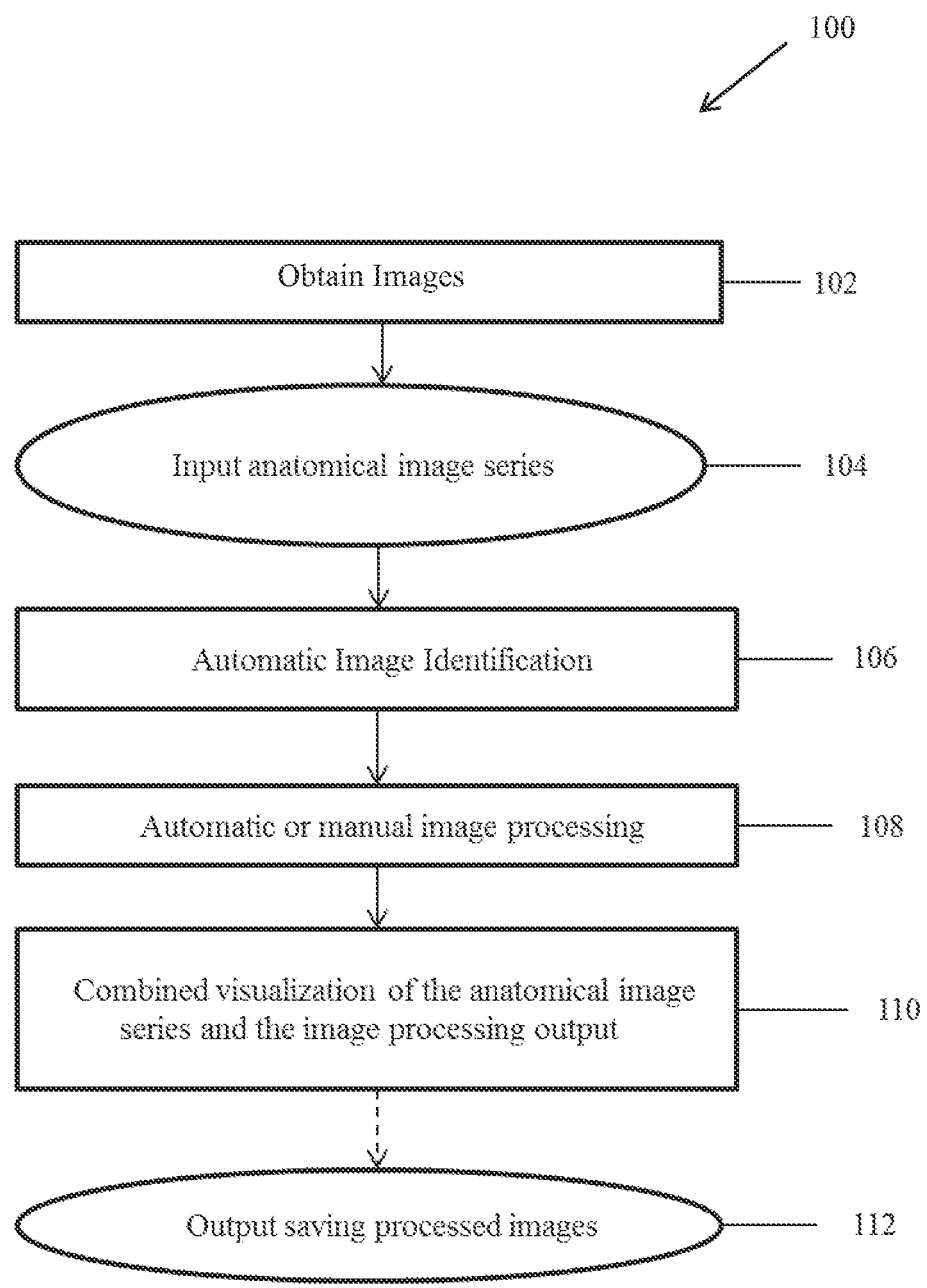
FIG. 2 is a flowchart of a method for automatically determining an image type in accordance with various embodiments.

FIG. 2 is a flowchart of a method 100 for automatically determining an image type in accordance with various embodiments. The method 100 may be implemented as a set of instructions on the image type recognition module 50 and/or the processor 28 both shown in FIG. 1. More specifically, the method 100 may be provided as a non-transitory machine-readable medium or media having instructions recorded thereon for directing the processor 28 or the image type recognition module 50 to perform an embodiment of the method described herein. The medium or media may be, for example, any type of CD-ROM, DVD, floppy disk, hard disk, optical disk, flash RAM drive, or other type of computer-readable medium or a combination thereof.

The method 100 automatically generates an image label, such as the DICOM tag 54 shown in FIG. 1 that is then automatically applied to or associated with an image, such as at least one of the images 52, also shown in FIG. 1, being displayed. As described above, the DICOM tag 54, in various embodiments, includes information that enables a clinician to identify the imaging modality utilized to generate the image and information that indicates whether the image includes information representative of a contrast agent.

Referring again to FIG. 2, at 102, a subject is scanned to generate a plurality of images, such as the series of images 52 shown in FIG. 1. In the illustrated embodiment, the series of images 52 are images acquired using the CT imaging system 10. In various other embodiments, the series of images 52 may be acquired using for example, the PET system 60, the ultrasound system 62, the x-ray system 64, the MR system 66, the SPECT system 68, and/or other imaging systems. Moreover, the series of images 52 may represent images acquired from more than one imaging modality. For example, the series of images 52 may include CT images, PET images, ultrasound images, x-ray images, MR images, or any combination thereof.

In various embodiments, a contrast agent may be injected into a patient. The patient may then be subsequently scanned to generate the series of images 52 or another series of images. In various other embodiments, the patient is not injected with the contrast agent prior to scanning the patient to generate the series of images 52. It should therefore be realized that in various embodiments, administering a contrast agent to the subject is optional.

Accordingly, it should be realized that although the method 100 is described with respect to the series of images 52 being obtained from the CT imaging system 10, the method 100 may also be applied to any images obtained from any imaging system. The various imaging systems described herein may be standalone imaging systems or form part of a multi-modality imaging system. Moreover, the method 100 may be applied to any images obtained using any of the imaging modalities discussed herein and the series of images 52 are exemplary only. Accordingly, in various embodiments, the series of images 52 is obtained using the CT imaging system 10 (shown in FIG. 1). In operation, the series of images may be obtained by performing a scan of the subject to produce the series of images 52. In various other embodiments, the series of images 52 may be obtained from data collected during a previous scan of the subject, wherein the series of images 52 have been stored in a memory. The series of images 52 may be obtained during real-time scanning of the subject. For example, the methods described herein may be performed on images as the images are received from the imaging system 10 during a real-time examination of the subject.

At 104, a series of images are input to, for example, the image type recognition module 50 for processing as is described in more detail below. In various embodiments, the user may select the series of images desired for subsequent processing. For example, the user may select the series of images 52 for subsequent processing or the user may select any other series of images for processing.

At 106, an image type is automatically determined. In various embodiments, the image type recognition module 50 is configured to automatically perform the image identification once the series of images are input to the image type recognition module. Moreover, in various embodiments, the image type recognition module 50 is configured to process the images as described herein in the background, for example at night or when the computation resources are available. In various other embodiments, the image type recognition module 50 is configured to automatically perform the image identification when a user initiated program has been activated. For example, when a user activates a segmentation program, the image type recognition module 50 is configured to automatically perform the image identification.

Figure 3:
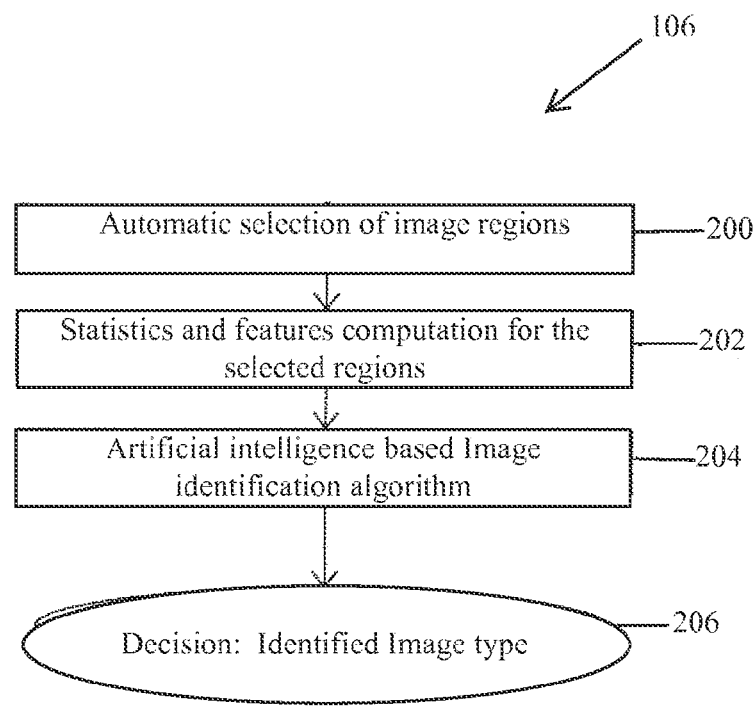
FIG. 3 is a flowchart of a method for performing a portion of the method shown in FIG. 2 in accordance with various embodiments.

FIG. 3 is a flowchart for automatically performing the automatic image identification shown at 106. At 200, anatomical regions within the series of images 52 are automatically selected. For example, the image type recognition module 50 may be configured to divide a single image in the series of images 52 into a set of sub-regions. For example, assume that the series of images 52 are acquired of a human torso. Accordingly, at 200, the image type recognition module 50 may be configured to divide the torso region into four sub-regions, wherein each sub-region represents a different area of the torso. For example, the image type recognition module 50 may be configured to divide the torso region into four substantially square sub-regions, wherein each sub-region represents a different area of the torso. The sub-regions may be displayed using bounding boxes that circumscribe the four sub-regions. Moreover, in various embodiments, the sub-regions each are formed to be substantially the same size, i.e. include the same number of pixels.

At 202, statistics and features are calculated for each of the sub-regions defined at 200. The statistics may include, for example, pixel intensity, average pixel intensity, mean pixel intensity, edges of various anatomical features, texture, etc. The features may include, for example, horizontal and vertical edge around the region, etc.

At 204, an artificial intelligence based algorithm is utilized to perform image identification. More specifically, the artificial intelligence based algorithm is configured to utilize the various statistics calculated at 202 to identify the imaging modality utilized to generate the image being analyzed. More specifically, the algorithm may utilize artificial intelligence (AI) sub-algorithms to identify the imaging modality utilized to generate the image being analyzed and whether the image is contrast enhanced. In various embodiments, the algorithm may be trained using a large set of known images to generate a training dataset. The training dataset may then be utilized to train the algorithm to identify various characteristics that enable the algorithm to determine the modality utilized to generate the image. Accordingly, in operation, the training dataset may include information of the shape of exemplary organ, expected outlines of various organs, expected pixel intensity values, etc. The known values in the training dataset may then be compared to the statistics generated at 202 to identify the type of image, i.e. the imaging system utilized to generate the image. The training datasets may also be obtained using automatic information gathering techniques. For example, the training dataset may be formed by compiling statistics of a plurality of images generated using a plurality of different imaging systems.

At 208, the results of the AI based algorithm are generated. In various embodiments, the results generated include an image type. For example, as discussed above, the image type may be a CT image, a PET image, an MR image, an ultrasound image, an x-ray image, etc. Moreover, the results include information indicating whether the image was acquired using a contrast agent acquired without the use of a contrast agent.

Figure 4:
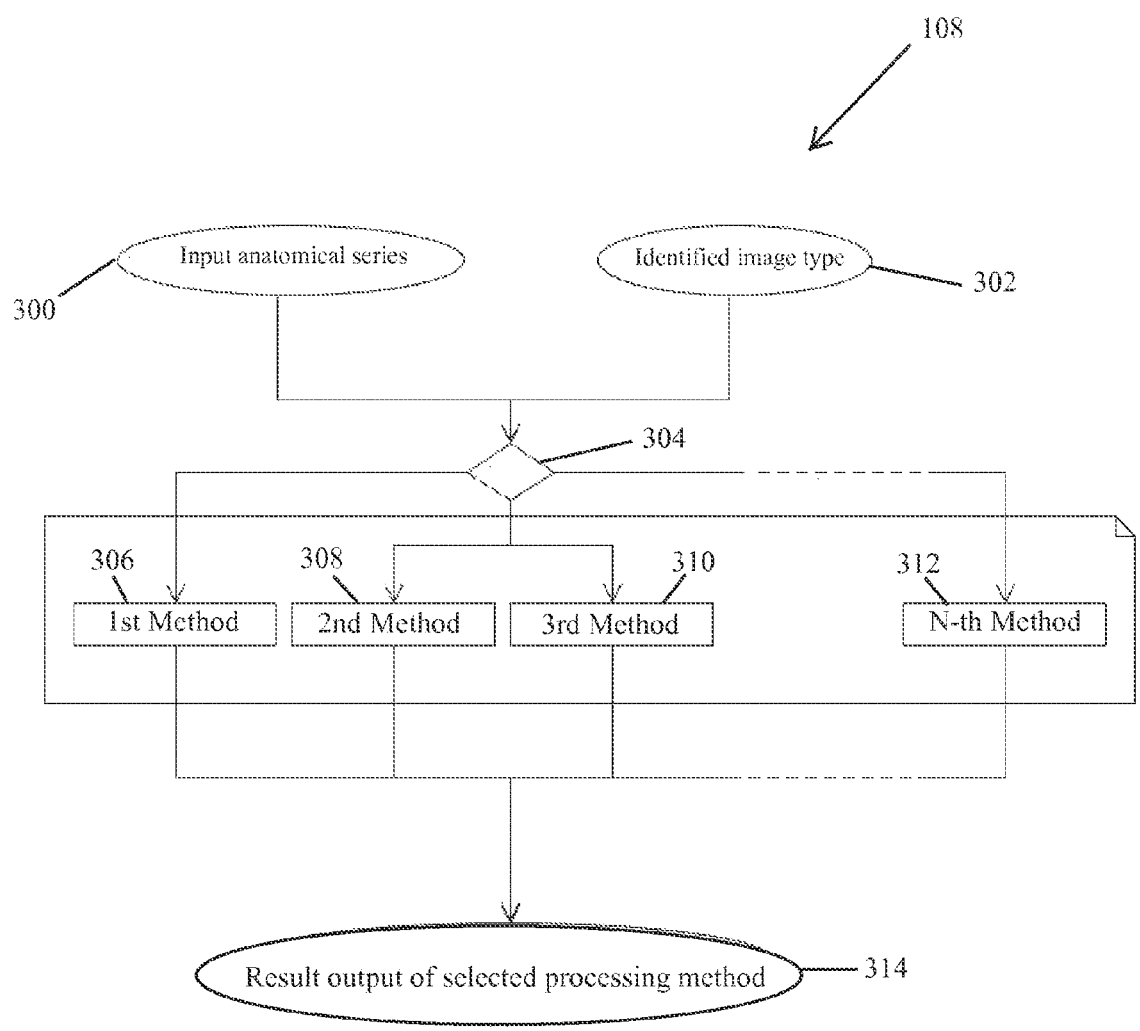
FIG. 4 is a flowchart of a method for performing a portion of the method shown in FIG. 2 in accordance with various embodiments.

Referring again to FIG. 2, at 108 automatic and/or manual imaging processing is performed using the series of images 152 and the image type information acquired at 206. FIG. 4 is a flowchart for performing the automatic or manual image processing of step 108. In various embodiments, the image processing techniques described herein may be implemented using for example, the processor 28 or the image type recognition module 50, each shown in FIG. 1. At 300, the series of images 152 are input to the image type recognition module 50. Additionally, at 302 the image type information and the contrast information determined at 206, for each image in the series of images 152 is also input to the image type recognition module 50.

At 304 a method of processing the series of images 52 is automatically selected based on the image type information and the contrast information received at 302. More specifically, the series of images 52 may be processed using a procedure selected from a plurality of procedures that may be utilized depending on the modality utilized to acquire the images and/or the presence or absence of a contrast agent. The plurality of procedures may include various segmentation algorithms wherein each of the segmentations algorithms is optimized to perform a segmentation procedure on a particular image type and/or contrast agent. For example, the segmentation algorithms may include a segmentation algorithm specifically configured for a contrast enhanced liver segmentation, a different segmentation algorithm specifically configured for non-contrast enhanced liver segmentation, etc.

Accordingly, at 304 the image type recognition module 50 utilizes the image type information and the information that represents the presence or absence of a contrast agent to automatically select an image processing procedure to be performed on the series of images 52. For example, in various embodiments, the image type recognition module 50 may automatically select a liver segmentation algorithm at 306, a non-contrast spleen segmentation at 308, a kidney segmentation at 310 or any other segmentation at 312. It should be realized the segmentation procedure is specifically selected based on the image type and the presence or absence of a contrast agent. Moreover, it should be realized that while various embodiments describe a segmentation procedure, any image processing procedure may be automatically performed on the series of images 52 and the segmentation procedure described herein is exemplary only. At 314, the post-processed images are displayed to the clinician. Thus, in various embodiments, once the series of images is selected, the methods and systems described herein are configured to automatically determine an image type, the presence or absence of a contrast agent, and select an appropriate image processing procedure based on the image type and the presence or absence of the contrast agent, and then automatically display the results to the user.

Referring again to FIG. 2, at 110, the post-processed images generated at 314 are displayed to the user. In various embodiments, the displayed images include the label 54 that indicates the image type and the presence or absence of the contrast agent. At 112, the post-processed images generated at 314 may be saved to a storage medium.

Figure 5:
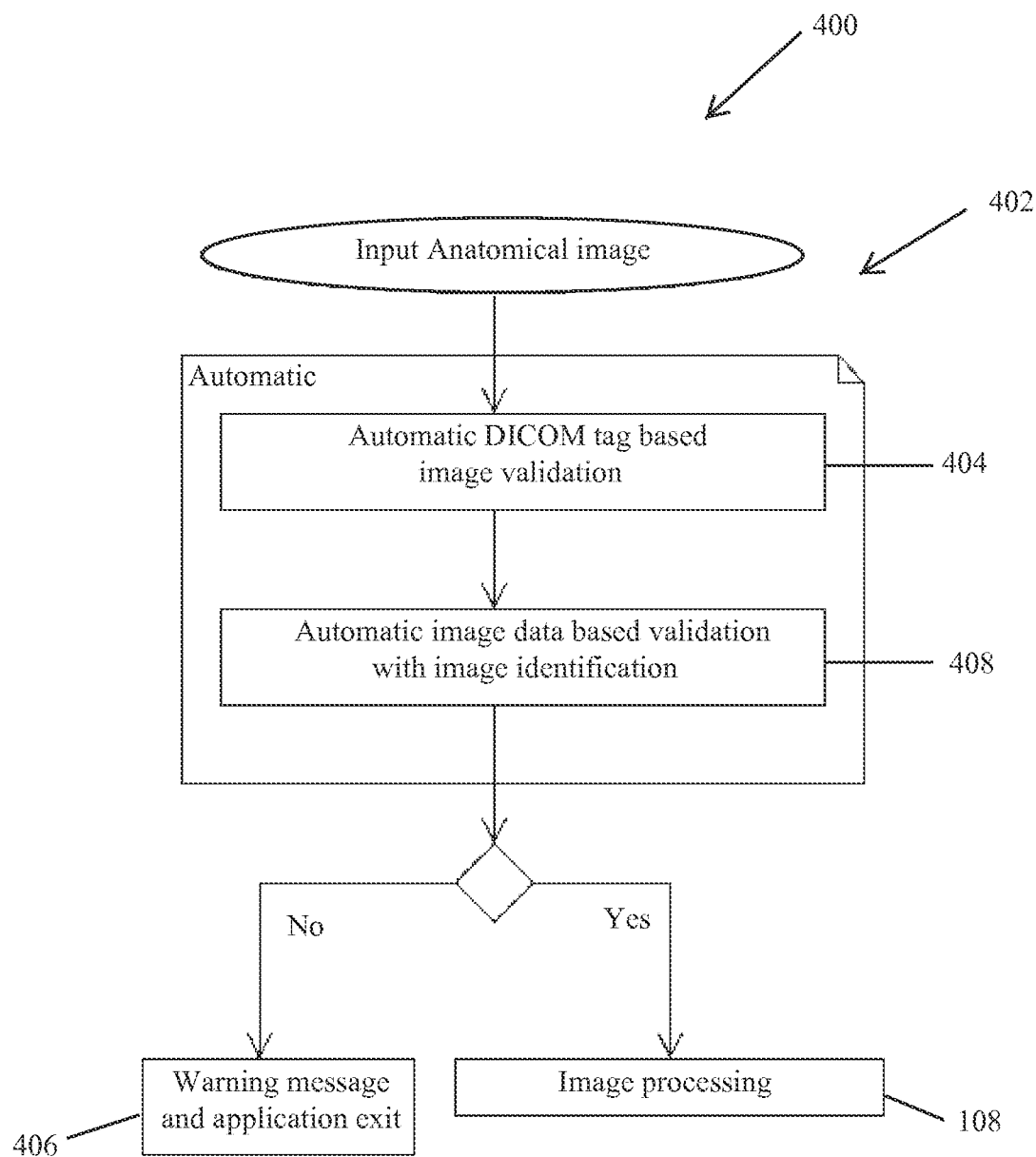
FIG. 5 is a flowchart of a method for performing a portion of the method shown in FIG. 2 in accordance with various embodiments.

FIG. 5 is a flowchart of an exemplary method 400 for automatically forming a label, such as the label 54 on an image in the series of images 52. In various embodiments, the label 54 is a DICOM tag that includes the image type and an indication that represents the presence or absence of the contrast agent. Moreover, in various embodiments, the method 400 may be utilized to check or confirm the existence of DICOM tags that were previously assigned to the images based on, for example, a manual user input which is some examples may be incorrect.

At 402, a series of images are input to, for example, the image type recognition module 50 for processing as is described in more detail below. In various embodiments, the user may select the series of images desired for subsequent processing. For example, the user may select the series of images 52 for subsequent processing or the user may select any other series of images for processing.

At 404, an automatic DICOM tag based image validation is implemented. In various embodiments, the information generated at step 304, which includes the image type information and the information and information regarding the presence or absence of a contrast agent may be utilized to validate or invalidate the DICOM tag. More specifically, the methods described herein facilitate generating an image type and also information regarding the presence or absence of the contrast agent using the images themselves. Accordingly, the information generated using the images themselves may be utilized to validate a DICOM tag previously attached to an image by a user. In various embodiments, if the DICOM tag is consistent with the information generated at step 304, i.e. the DICOM tag is validated, the method 400 proceeds to proceeds to step 108 shown in FIG. 1 wherein image processing is performed. In various other embodiments, if the DICOM tag is not consistent with the information generated at step 304, i.e. the DICOM tag is not validated, the method 400 proceeds to proceeds to step 406 wherein a visual or audible indication is generated to inform the user that the DICOM tag is not consistent with information generated at step 304. Optionally, if the DICOM tag is not consistent with the information generated at step 304, i.e. the DICOM tag is not validated, the method 400 may cause the module 50 to discontinue implementation of the method 100.

At 408, automatic image data based safety checks are performed on the selected input image. More specifically, if the anatomical image is correct, the method 400 proceeds to proceeds to step 108 shown in FIG. 1 wherein image processing is performed.

Described herein are embodiments that are configured to automatically analyze an image to automatically generate information that is subsequently utilized to generate a label, such as a DICOM tag 54 that is automatically formed on or associated with the image. The DICOM tag 54 includes information that enables a clinician to identify the imaging modality utilized to generate the image and information that indicates whether the image includes information representative of a contrast agent. More specifically, in various embodiments, the methods and systems described herein are also enabled to identify an imaging protocol utilized to scan the subject. More specifically, the MR image contrast may be modified by changing the imaging protocol which sets the pulse sequence parameters. A pulse sequence sets the specific number, strength, and timing of the RF and gradient pulses. Accordingly, various imaging protocols that may be identified include. T1-weighted and T2-weighted spin-echo sequences, Fluid Attenuated Inversion Recovery (FLAIR), water, and fat, among others. Additionally, and in various embodiments, the methods and systems described herein are also enabled to identify the contrast agent, or biomarker, utilized during the imaging procedure. By way of example only, the imaging agent may be Myoview™, Fluorodeoxyglucose (FDG), $^{18}$F-Flourobenzyl Triphenyl Phosphonium ($^{18}$F-FBnTP), $^{18}$F-Flouroacetate, $^{18}$F-labeled myocardial perfusion tracers, Tc-ECD, Tc-HMPAO, N-13 ammonia, Envision N-13H3 Iodine-123 ligands, $^{99m}$-Technitium ligands, Xenon-133. Neuroreceptor ligands, etc.), 18F-fluoromisonidazole, $^{201}$Thallium, $^{99m}$Technetium sestamibi, and $^{82}$Rubidium an others.

Figure 6:
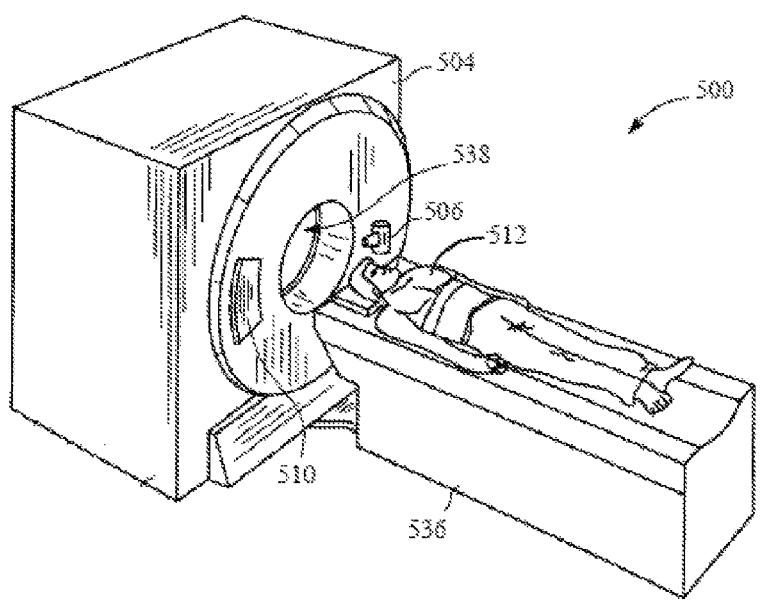
FIG. 6 is a pictorial drawing of a computed tomography (CT) imaging system constructed in accordance with various embodiments.
Figure 7:
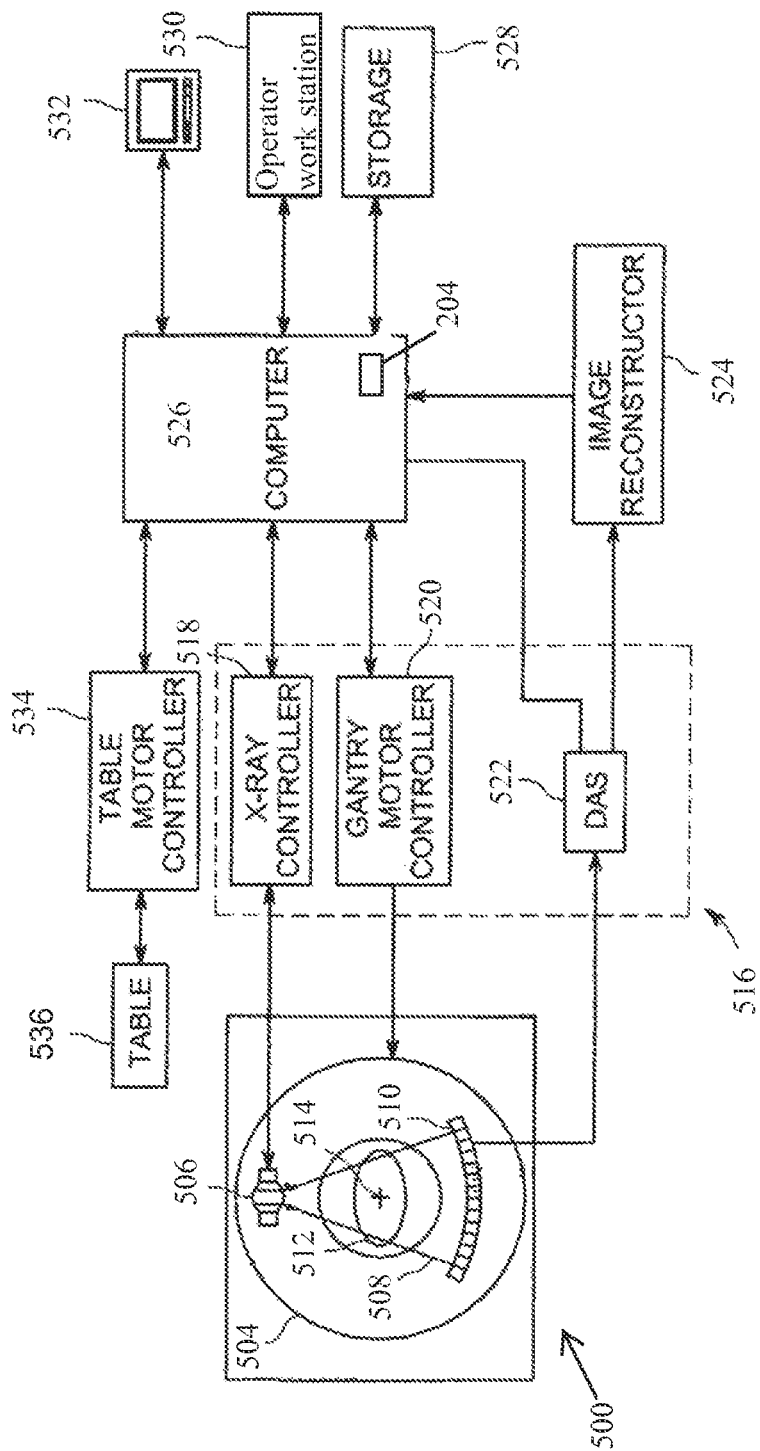
FIG. 7 is a schematic block diagram of the CT imaging system of FIG. 6.

The various methods and the image type recognition module 50 may be implemented in an exemplary imaging, system. The various methods and the module 50 may be implemented in an exemplary imaging system. For example. FIG. 6 is a pictorial view of an imaging system that is formed in accordance with various embodiments. FIG. 7 is a block schematic diagram of a portion of the imaging system shown in FIG. 6. Although various embodiments are described in the context of a CT imaging system, it should be understood that other imaging systems capable of performing the functions described herein are contemplated as being used.

Referring to FIGS. 6 and 7, the CT imaging system 500 includes a gantry 504, which includes an x-ray source 506 that projects a beam of x-rays 508 toward a detector array 510 on the opposite side of the gantry 504. The detector at 510 is formed by a plurality of detector rows (not shown) including a plurality of the detectors 502 that together sense the projected x-rays that pass through an object, such as a patient 512 that is disposed between the detector array 510 and the x-ray source 506. Each detector 502 produces an electrical signal that represents the intensity of an impinging x-ray beam and hence can be used to estimate the attenuation of the beam as the beam passes through the patient 512. During a scan to acquire x-ray projection data, the gantry 504 and the components mounted therein rotate about a center of rotation 514. FIG. 7 shows only a single row of detectors 502 (i.e., a detector row). However, the multi-slice detector array 510 includes a plurality of parallel detector rows of detectors 502 such that projection data corresponding to a plurality of quasi-parallel or parallel slices can be acquired simultaneously during a scan.

Rotation of components on the gantry 504 and the operation of the x-ray source 506 are controlled by a control mechanism 516 of the CT imaging system 500. The control mechanism 516 includes an x-ray controller 518 that provides power and timing signals to the x-ray source 506 and a gantry motor controller 520 that controls the rotational speed and position of components on the gantry 504. A data acquisition system (DAS) 522 in the control mechanism 516 samples analog data from the detectors 502 and converts the data to digital signals for subsequent processing. An image reconstructor 524 receives sampled and digitized x-ray data from the DAS 522 and performs high-speed image reconstruction. The reconstructed images, i.e. the series of images 52, are applied as an input to a computer 526 that stores the image in a storage device 528. The image reconstructor 524 can be specialized hardware or computer programs executing on the computer 526. In various embodiments, the computer 526 may include the image type recognition module 50 described above.

The computer 526 also receives commands and scanning parameters from an operator via an operator workstation 530 that has a keyboard and/or other user input and/or marking devices, such as a mouse, trackball, or light pen. An associated display 532, examples of which include a cathode ray tube (CRT) display, liquid crystal display (LCD), or plasma display, allows the operator to observe the reconstructed image and other data from the computer 526. The display 532 may include a user pointing device, such as a pressure-sensitive input screen. The operator supplied commands and parameters are used by the computer 526 to provide control signals and information to the DAS 522, the x-ray controller 518, and the gantry motor controller 520. In addition, the computer 526 operates a table motor controller 534 that controls a motorized table 536 to position the patient 512 in the gantry 504. For example, the table 536 moves portions of the patient 512 through a gantry opening 538.

Various embodiments described herein provide a tangible and non-transitory machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the described subject matter without departing from their scope. While the dimensions and types of materials described herein are intended to define the parameters of the various embodiments of the invention, the embodiments are by no means limiting and are exemplary embodiments. Many other embodiments will be apparent to one of ordinary skill in the art upon reviewing the above description. The scope of the various embodiments of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable one of ordinary skill in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for determining image information for an image of an object, said method comprising:
    obtaining at least one image of an object of interest;
    automatically determining an image type and a presence or absence of a contrast agent;
    automatically generating a label, wherein the label indicates the image type and at least one of the presence or absence of the contrast agent;
    automatically selecting an image processing procedure based on the image type and the presence or absence of the contrast agent;
    automatically implementing the selected image processing procedure on the at least one image; and
    modifying the at least one image to include the label.

2. The method of claim 1, wherein the image type includes at least one of a computed tomography (CT) image type, a positron emission tomography (PET) image type, an ultrasound image type, an x-ray image type, a magnetic resonance (MR) imaging type or a single photon emission computed tomography (SPECT) image type.

3. The method of claim 1, wherein automatically determining an image type comprises:
    automatically dividing the image into image sub-regions;
    automatically generating statistics of the sub-regions; and
    automatically determining the image type based on the statistics using an artificial intelligence algorithm.

4. A method for determining image information for an image of an object, said method comprising:
    obtaining at least one image of an object of interest;
    automatically determining an image type and a presence or absence of a contrast agent;
    automatically generating a label, wherein the label indicates the image type and at least one of the presence or absence of the contrast agent;
    automatically selecting a segmentation procedure based on the image type and the presence or absence of the contrast agent;
    automatically implementing the selected segmentation procedure on the at least one image; and
    modifying the at least one image to include the label.

5. A method for determining image information for an image of an object, said method comprising:
    obtaining at least one image of an object of interest;
    automatically determining an image type and a presence or absence of a contrast agent;
    automatically generating a label, wherein the label indicates the image type and at least one of the presence or absence of the contrast agent;
    automatically comparing the label to a second label previously formed on the image;
    automatically replacing the second label based on the comparison; and
    modifying the at least one image to include the label.

6. A method for determining image information for an image of an object, said method comprising:
    obtaining at least one image of an object of interest;
    automatically determining an image type and a presence or absence of a contrast agent;
    automatically generating a label, wherein the label indicates the image type and at least one of the presence or absence of the contrast agent;
    automatically comparing the label to a second label previously formed on the image;
    automatically generating a warning if the label is not the same as the second label; and
    modifying the at least one image to include the label.

7. An imaging system comprising:
    an imaging scanner; and
    a processor coupled to the imaging scanner, the processor configured to:
        obtain at least one image of an object of interest;
        automatically determine an image type and a presence or absence of a contrast agent;
        automatically generate a label, wherein the label indicates the image type and at least one of the presence or absence of the contrast agent;
        automatically select an image processing procedure based on the image type and the presence or absence of the contrast agent; and
        automatically implement the selected image processing procedure on the at least one image; and
        modify the at least one image to include the label.

8. The imaging system of claim 7, wherein the image type includes at least one of a computed tomography (CT) image type, a positron emission tomography (PET) image type, an ultrasound image type, an x-ray image type, a magnetic resonance (MR) imaging type or a single photon emission computed tomography (SPECT) image type.

9. The imaging system of claim 7, wherein the processor is further configured to:
    automatically divide the image into image sub-regions;
    automatically generate statistics of the sub-regions; and
    determine the image type based on the statistics using an artificial intelligence algorithm.

10. An imaging system comprising:
an imaging scanner; and
a processor coupled to the imaging scanner, the processor configured to:
    obtain at least one image of an object of interest;
    automatically determine an image type and a presence or absence of a contrast agent;
    automatically generate a label, wherein the label indicates the image type and at least one of the presence or absence of the contrast agent;
    automatically select a segmentation procedure based on the image type and the presence or absence of the contrast agent;
    automatically implement the selected segmentation procedure on the at least one image; and
    modify the at least one image to include the label.

11. An imaging system comprising:
an imaging scanner; and
a processor coupled to the imaging scanner, the processor configured to:
    obtain at least one image of an object of interest;
    automatically determine an image type and a presence or absence of a contrast agent;
    automatically generate a label, wherein the label indicates the image type and at least one of the presence or absence of the contrast agent;
    automatically compare the label to a second label previously formed on the image;
    automatically replace the second label based on the comparison; and
    modify the at least one image to include the label.

12. An imaging system comprising:
an imaging scanner; and
a processor coupled to the imaging scanner, the processor configured to:
    obtain at least one image of an object of interest;
    automatically determine an image type and a presence or absence of a contrast agent;
    automatically generate a label, wherein the label indicates the image type and at least one of the presence or absence of the contrast agent;
    automatically compare the label to a second label previously formed on the image;
    automatically generate a warning if the label is not the same as the second label and
    modify the at least one image to include the label.

13. A non-transitory computer readable medium storing a computer program to instruct a computer to:
    obtain at least one image of an object of interest;
    automatically determine an image type and a presence or absence of a contrast agent;
    automatically generate a label, wherein the label indicates the image type and at least one of the presence or absence of the contrast agent;
    automatically select an image processing procedure based on the image type and the presence or absence of the contrast agent;
    automatically implement the selected image processing procedure on the at least one image; and
    modify the at least one image to include the label.

14. The non-transitory computer readable medium storing a computer program of claim 13, wherein the image type includes at least one of a computed tomography (CT) image type, a positron emission tomography (PET) image type, an ultrasound image type, an x-ray image type, a magnetic resonance (MR) imaging type or a single photon emission computed tomography (SPECT) image type.

15. The non-transitory computer readable medium storing a computer program of claim 13, further programmed to instruct the computer to
    automatically divide the image into image sub-regions;
    automatically generate statistics of the sub-regions; and
    determine the image type based on the statistics using an artificial intelligence algorithm.

16. A non-transitory computer readable medium storing a computer program to instruct a computer to:
    obtain at least one image of an object of interest;
    automatically determine an image type and a presence or absence of a contrast agent;
    automatically generate a label, wherein the label indicates the image type and at least one of the presence or absence of the contrast agent;
    automatically select a segmentation procedure based on the image type and the presence or absence of the contrast agent;
    automatically implement the selected segmentation procedure on the at least one image; and
    modify the at least one image to include the label.

17. A non-transitory computer readable medium storing a computer program to instruct a computer to:
    obtain at least one image of an object of interest;
    automatically determine an image type and a presence or absence of a contrast agent;
    automatically generate a label, wherein the label indicates the image type and at least one of the presence or absence of the contrast agent;
    automatically compare the label to a second label previously formed on the image;
    automatically replace the second label based on the comparison; and
    modify the at least one image to include the label.

* * * * *